US00PP12071P2

(12) United States Plant Patent
Daniel, 3rd

(10) Patent No.: US PP12,071 P2
(45) Date of Patent: Aug. 28, 2001

(54) ILEX PLANT NAMED 'THEO'

(76) Inventor: Theo S. Daniel, 3rd, 4022 CR 4709, Athens, TX (US) 75751

( * ) Notice: Subject to any disclaimer, the term of this patent is extended or adjusted under 35 U.S.C. 154(b) by 0 days.

(21) Appl. No.: 09/519,434

(22) Filed: Mar. 6, 2000

(51) Int. Cl.[7] ..... A01H 5/00
(52) U.S. Cl. ..... Plt./247
(58) Field of Search ..... Plt./247, 226

(56) References Cited

U.S. PATENT DOCUMENTS

P.P. 8,779 * 6/1994 Pittman ..... Plt./247
P.P. 9,543 * 5/1996 Daniel, 3rd ..... Plt./247
P.P. 10,295 * 3/1998 Wilkins ..... Plt./247

* cited by examiner

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Ilex plant named 'Theo', characterized by its semi-dwarf and upright plant habit; dark green rounded leaves; short lateral branches with short internodes; freely branching habit; red-colored drupes; tolerance to freezing temperatures; and high rooting percentage.

2 Drawing Sheets

BACKGROUND OF THE INVENTION

The present Invention relates to a new and distinct cultivar of Ilex plant, botanically known as *Ilex vomitoria*, and hereinafter referred to by the cultivar name 'Theo'.

The new Ilex originated from a self-pollination of an unidentified selection of *Ilex vomitoria* in 1935. The cultivar Theo was discovered and selected by the Inventor as a single plant within a population of 10,000 progeny in a controlled environment in Athens, Tex., in 1946. The selection of this plant was based on its semi-dwarf plant habit, short lateral branches with short internodes, dark green rounded leaves, large number of drupes, and tolerance to freezing temperatures in comparison to plants of the parent selection.

Asexual reproduction of the new cultivar by terminal cuttings taken at Athens, Tex., since 1947, has shown that the unique features of this new Ilex are stable and reproduced true to type in successive generations of asexual reproduction.

SUMMARY OF THE INVENTION

The following traits have been repeatedly observed and are determined to be the unique characteristics of 'Theo'. These characteristics in combination distinguish 'Theo' as a new and distinct cultivar:

1. Semi-dwarf and upright plant habit.
2. Dark green rounded leaves.
3. Short lateral branches with short internodes; densely foliated.
4. Freely branching habit.
5. Red-colored drupes.
6. Tolerance to freezing temperatures.
7. Relatively high percentage of successfully rooted cuttings.

Plants of the new Ilex can be compared to plants of the nonpatented *Ilex vomitoria* cultivar 'Pride of Houston'. In side-by-side comparisons conducted by the Inventor in Athens, Tex., plants of the new Ilex differed from plants of the cultivar 'Pride of Houston' in the following characteristics:

1. Plants of the new Ilex are shorter than plants of the cultivar 'Pride of Houston'.
2. Plants of the new Ilex have darker green and more rounded leaves than plants of the cultivar 'Pride of Houston'.
3. Plants of the new Ilex have shorter lateral branches and shorter internodes than plants of the cultivar 'Pride of Houston'.
4. Plants of the new Ilex produce more drupes per plant than plants of the cultivar 'Pride of Houston'.
5. Plants of the new Ilex are more tolerant to freezing temperatures than plants of the cultivar 'Pride of Houston'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Ilex.

The photograph on the first sheet comprises a side perspective view of a typical plant of 'Theo'.

The photograph at the top of the second sheet comprises a close-up view of typical leaves.

The photograph at the bottom of the second sheet comprise a close-up view of typical leaves and immature and mature drupes of 'Theo'.

DETAILED BOTANICAL DESCRIPTION

Plants of the cultivar 'Theo' have not been observed under all possible environmental conditions. The phenotype may vary somewhat with variations in environment such as temperature and light intensity, without, however, any variance in genotype. The following observations, measurements and comparisons describe plants grown in San Antonio and Keller, Tex., under outdoor conditions which closely approximate commercial production conditions. Plants used for the descriptions were grown in 25-cm containers and were about three years old.

In the following description, color references are made to The Royal Horticultural Society Colour Chart except where general terms of ordinary dictionary significance are used.

Botanical classification: *Ilex vomitoria* cultivar 'Theo'.

Parentage: Random self-pollinations of an unidentified selection of *Ilex vomitoria*.

Propagation:

*Type cutting.*—Terminal cuttings.

*Time to initiate roots.*—Summer: About 56 to 70 days at 29° C. Winter: About 70 to 140 days at 16° C.

*Time to produce a rooted cutting or liner.*—Summer: About 140 to 165 days at 29° C. Winter: About 165 to 196 days at 16° C.

*Root description.*—Fibrous, freely branching. Relatively high percentage of successfully rooted cuttings.

Plant description:

*General appearance/growth habit.*—Perennial semi-dwarf, evergreen shrub; upright, columnar.

*Branching habit.*—Responds well to pruning; freely branching, lateral branches potentially developing at evey node after removal of terminal apex.

*Plant height.*—About 1.5 m.

*Plant width.*—About 53 cm.

*Lateral branch description.*—Length: About 18 cm. Diameter: About 5 mm. Internode length: About 3 mm, very closely spaced. Color: Woody: Close to 197A to 197B. Young: Close to 197B. Texture: Smooth.

*Foliage description.*—Leaves simple, alternate; generally symmetrical; abundant, densely foliated. Length: About 2.6 cm. Width: About 1.7 cm. Shape: Rounded oblong. Apex: Rounded. Base: Obtuse. Margin: Crenate. Texture: Leathery, tough, very durable; glabrous. Color: Young foliage, upper surface: 144A to 137A to 147A. Young foliage, lower surface: Close to 147B. Fully expanded foliage, upper surface: 147A. Fully expanded foliage, lower surface: 147B. Petiole: Length: About 5 mm. Diameter: Less than 1 mm. Color: Close to 144A.

Flower description: Typical of species.

*Natural flowering season.*—Spring.

*Flower arrangement/type.*—Male flowers in fascicles; female flowers typically solitary; 4-merous; corolla round; petals (both surfaces) white, close to 155D; flowers persistent.

*Reproductive organs.*—Typical of the species.

*Drupes.*—Shape: Spherical. Diameter: About 7 mm. Color: Immature: Close to 144A. Mature: 45A to 46A.

Low temperature tolerance: Plants of the new Ilex are tolerant to freezing temperatures.

Disease resistance: Plants of the new Ilex have demonstrated good resistance to pathogens common to Ilex.

It is claimed:

1. A new and distinct cultivar of Ilex plant named 'Theo', as illustrated and described.

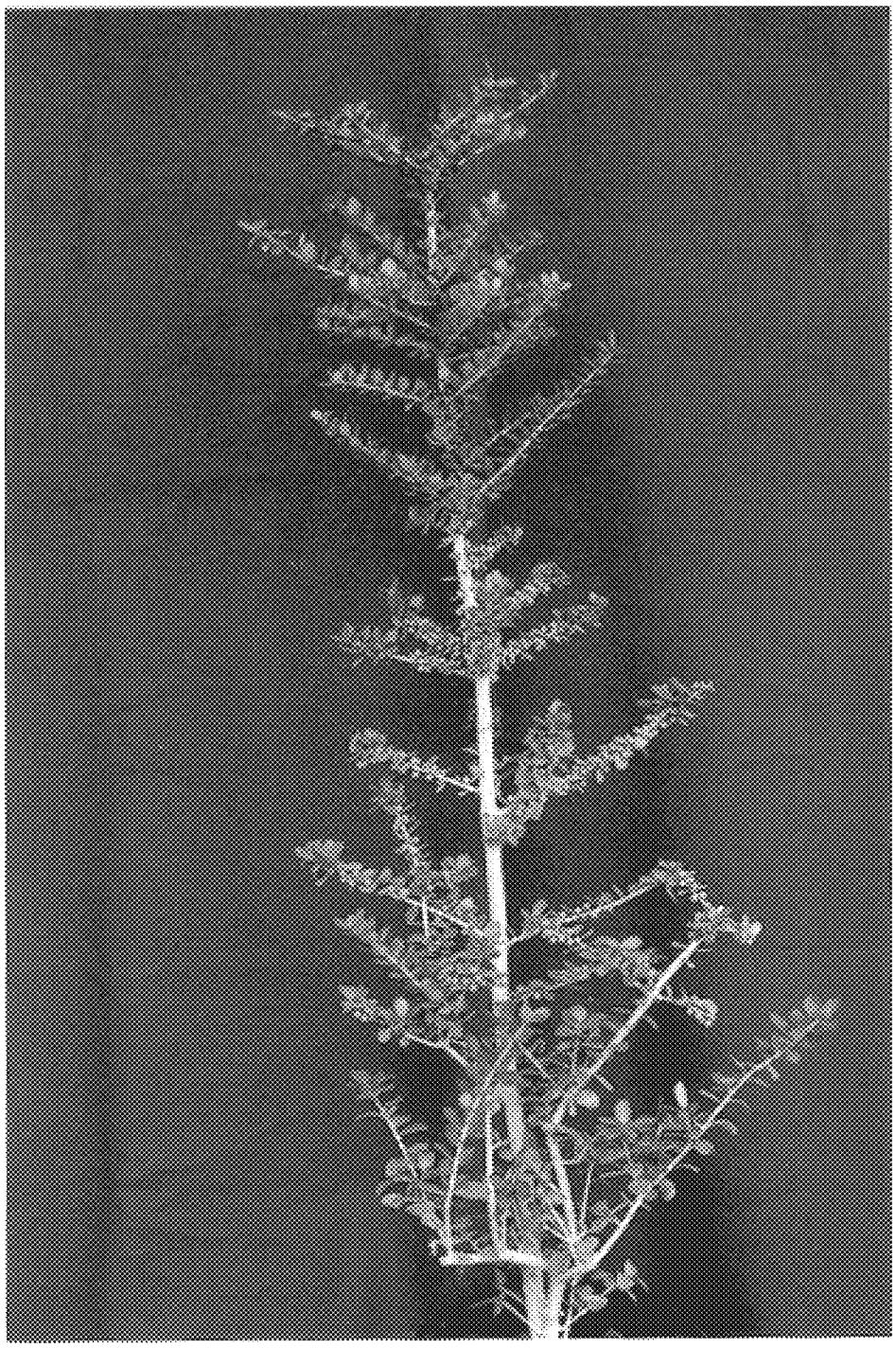

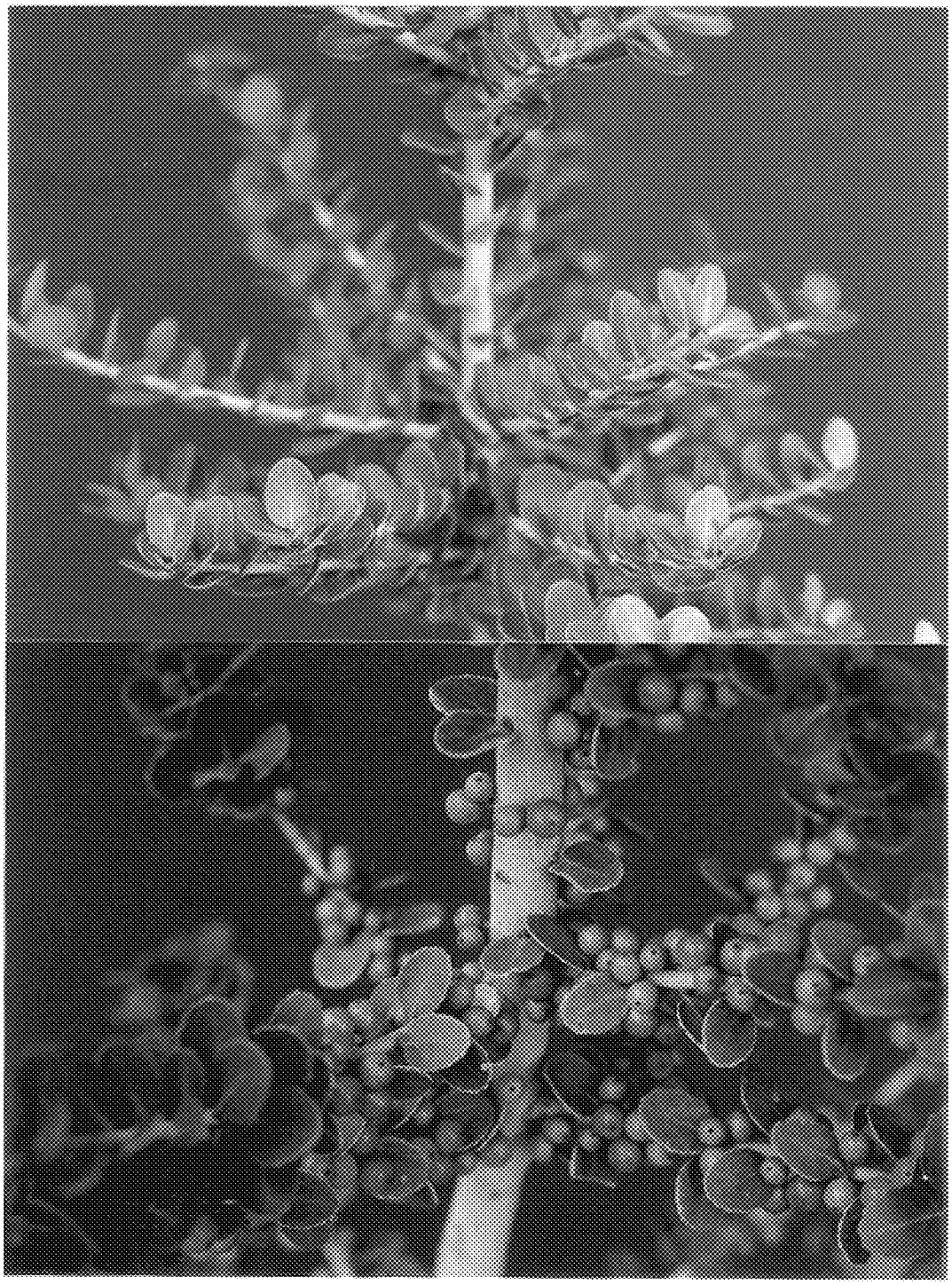

* * * * *